United States Patent
Matsumoto et al.

(10) Patent No.: US 10,413,701 B2
(45) Date of Patent: Sep. 17, 2019

(54) MEDICAL TUBE

(71) Applicant: KANEKA CORPORATION, Osaka-shi, Osaka (JP)

(72) Inventors: Mariko Matsumoto, Settsu (JP); Yoichi Matsumura, Settsu (JP); Hidekazu Miyauchi, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 765 days.

(21) Appl. No.: 14/374,623

(22) PCT Filed: Jan. 25, 2013

(86) PCT No.: PCT/JP2013/051561
§ 371 (c)(1),
(2) Date: Jul. 25, 2014

(87) PCT Pub. No.: WO2013/111848
PCT Pub. Date: Aug. 1, 2013

(65) Prior Publication Data
US 2015/0018962 A1    Jan. 15, 2015

(30) Foreign Application Priority Data
Jan. 26, 2012 (JP) ................................. 2012-014592

(51) Int. Cl.
 *C10M 139/00*    (2006.01)
 *C10M 159/18*    (2006.01)
(Continued)

(52) U.S. Cl.
CPC ....... *A61M 25/0045* (2013.01); *A61F 2/0077* (2013.01); *A61F 2/82* (2013.01);
(Continued)

(58) Field of Classification Search
CPC .. A61M 2025/0047; A61M 2025/0046; C10M 7/00; C08L 75/04
(Continued)

(56) References Cited

U.S. PATENT DOCUMENTS 5,077,352 A    12/1991 Elton
6,020,071 A    2/2000 Watson
(Continued)

FOREIGN PATENT DOCUMENTS

EP    2 172 232 A1    4/2010
EP    2172232 A1 *    4/2010    ........... A61L 29/085
(Continued)

OTHER PUBLICATIONS

International Search Report issued in PCT/JP2013/051561, dated Mar. 19, 2013.
(Continued)

*Primary Examiner* — Prem C Singh
*Assistant Examiner* — Francis C Campanell
(74) *Attorney, Agent, or Firm* — Birch, Stewart, Kolasch & Birch, LLP (57) ABSTRACT

A medical tube in which an intermediate layer composed of a composition containing (a), (b), and (c1) listed below and a lubricant layer composed of a composition containing (a), (b), and (c2) listed below are sequentially laminated on a surface of an insertion member to be inserted into a living body: (a) 1 to 35 weight % of at least one of aromatic diisocyanate, aliphatic diisocyanate, and alicyclic diisocyanate; (b) 1 to 35 weight % of trifunctional or higher functionality polyol; (c1) 30 to 98 weight % of polyalkylene glycol and/or monomethoxypolyalkylene glycol; and (c2) 30 to 98 weight % of polyalkylene glycol (including polyalkylene glycol larger in weight-average molecular weight than polyalkylene glycol in (c1)) and/or monomethoxypoly-
(Continued)

alkylene glycol (including monomethoxypolyalkylene glycol larger in weight-average molecular weight than monomethoxypolyalkylene glycol in (c1)),
(where each of the glycols in (c1) and (c2) is diol).

19 Claims, 3 Drawing Sheets

(51) Int. Cl.

| | | |
|---|---|---|
| *C10M 137/10* | (2006.01) | |
| *B32B 27/00* | (2006.01) | |
| *B32B 27/40* | (2006.01) | |
| *A61M 25/00* | (2006.01) | |
| *A61L 29/08* | (2006.01) | |
| *A61L 29/14* | (2006.01) | |
| *A61F 2/00* | (2006.01) | |
| *A61F 2/82* | (2013.01) | |
| *B05D 1/02* | (2006.01) | |
| *B05D 1/18* | (2006.01) | |
| *B05D 1/28* | (2006.01) | |
| *A61F 9/007* | (2006.01) | |

(52) U.S. Cl.
CPC ............ *A61L 29/085* (2013.01); *A61L 29/14* (2013.01); *B05D 1/02* (2013.01); *B05D 1/18* (2013.01); *B05D 1/28* (2013.01); *A61F 9/00772* (2013.01); *A61F 2210/0076* (2013.01); *A61L 2400/10* (2013.01); *A61L 2420/08* (2013.01); *A61M 25/0009* (2013.01); *A61M 2025/0046* (2013.01); *A61M 2207/00* (2013.01)

(58) Field of Classification Search
USPC .............................. 508/100, 386; 428/423.1
See application file for complete search history.

(56) References Cited

U.S. PATENT DOCUMENTS

| | | |
|---|---|---|
| 2009/0270291 A1 | 10/2009 | Matsumura et al. |
| 2010/0174235 A1 | 7/2010 | Yamaguchi |

FOREIGN PATENT DOCUMENTS

| | | |
|---|---|---|
| JP | 4-227671 A | 8/1992 |
| JP | 2539325 B2 | 10/1996 |
| JP | 11-506375 A | 6/1999 |
| JP | 2001-104485 A | 4/2001 |
| JP | 2010-246857 A | 11/2010 |
| JP | 2011-200601 A | 10/2011 |
| WO | WO 96/39204 A1 | 12/1996 |
| WO | WO 2006/095766 A1 | 9/2006 |
| WO | WO 2008/023696 A1 | 2/2008 |
| WO | WO 2008/156132 A1 | 12/2008 |

OTHER PUBLICATIONS

Yabe et al., "The Effectiveness and Clinical Applications of a Hydrophilic Heparinized Polyurethane Lacrimal Stent Tube", Japanese Journal of Ophthalmic Surgery, vol. 21, No. 2, 2008, pp. 237-242.

* cited by examiner

MEDICAL TUBE

TECHNICAL FIELD

The present invention relates to a medical tube that is inserted into a living body, for example, a lacrimal duct, a blood vessel, and the like.

BACKGROUND ART

Conventionally, it has been widely employed a medical tube to be inserted into a portion of a living body such as a lumen, which has a layer with lubricity (lubricant layer) on the surface of an insertion member to be inserted into a living body. It is considered that forming such a layer reduces resistance of contact between the insertion member inserted into the living body and the living body, which makes it possible to improve insertability of the medical tube and alleviate distress in a patient and damage to the body of the patient.

In what follows, taking as examples treatments for lacrimal duct obstruction, intravascular disease, and the like in which a treatment tube with the lubricant layer may be used, background arts of lacrimal duct tube and occlusion catheter for use in these treatments and the like will be described.

First, the lacrimal duct tube will be described. The lacrimal duct tube is a treatment tube for use in treatment of lacrimal duct obstruction resulting in epiphora.

Treatment methods for lacrimal duct obstruction include: (i) probing by a lacrimal duct bougie, (ii) placement of a lacrimal duct tube; (iii) dacryocystorhinostomy (DCR); (iv) lacrimal canaliculoplasty; (v) nasolacrimal duct plasty; (vi) lacrimal caruncle moving surgery, and the like.

The (i) probing by a lacrimal duct bougie is intended to insert a narrow tube called bougie into a lacrimal duct to open an obstructed site and reconstruct a flow path for a lacrimal fluid. The (ii) lacrimal duct tube to be used after that is a lacrimal duct intubation instrument to be placed to keep the flow path and reconstruct tissues. These treatments are conducted as first treatments in many cases due to their ease of execution and minimal invasiveness.

The (iii) dacryocystorhinostomy (DCR), (iv) lacrimal canaliculoplasty, (v) nasolacrimal duct plasty, and (vi) lacrimal caruncle moving surgery are highly effective but relatively invasive because of the need for creation of incisions in a patient's face or drilling holes in bones, and thus are conducted as a last resort.

Figure 2:
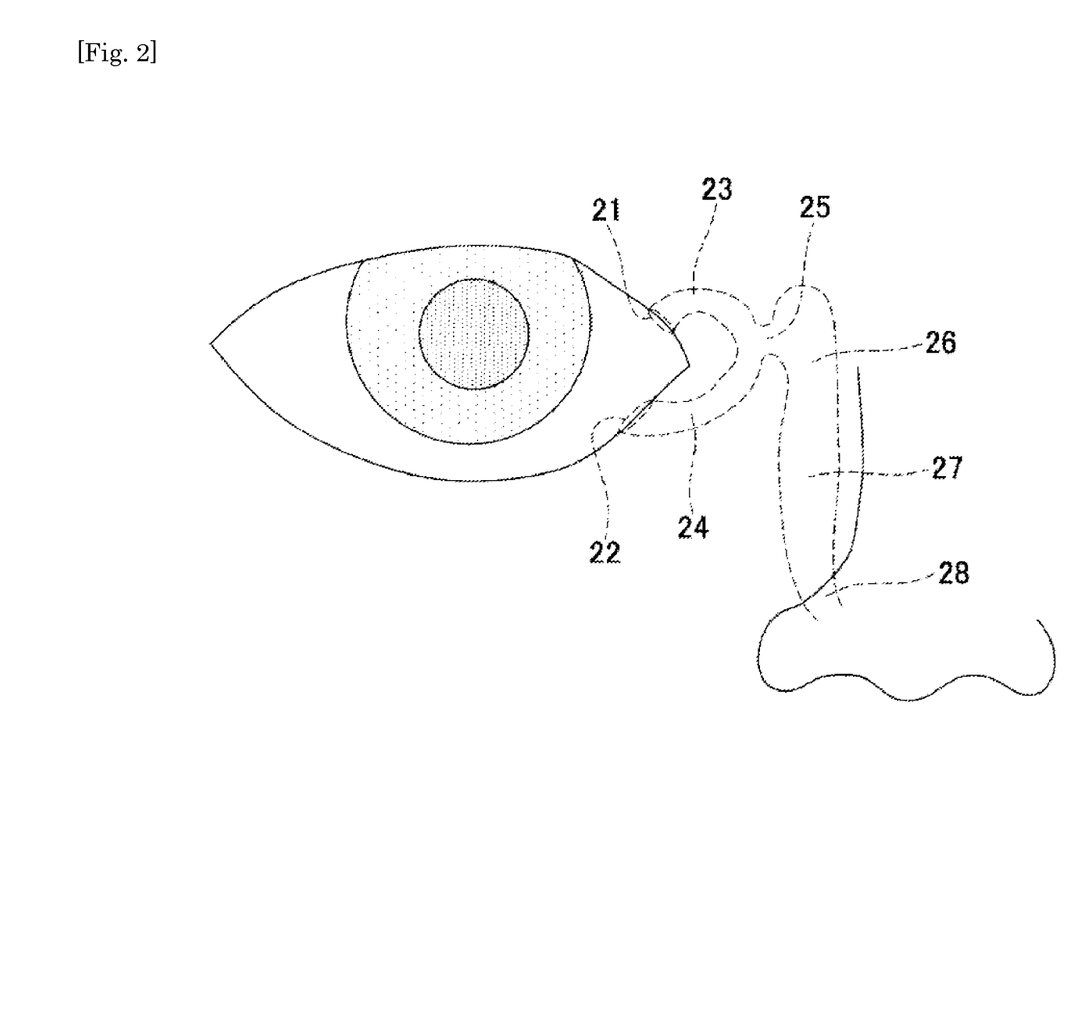
FIG. 2 is an illustrative diagram showing an anatomic structure of a lacrimal duct.

As a lacrimal duct tube used in (ii), a so-called nunchaku-shaped lacrimal duct tube is widely available (Patent Document 1). The nunchaku-shaped lacrimal duct tube includes a tube and a pair of bougies that is inserted from cuts at both sides of the tube, and the bougies are operated to guide the lacrimal duct tube into a lacrimal duct and place the tube there. As shown in FIG. 2, a lacrimal duct is formed by lacrimal punctum (21 and 22), lacrimal canaliculus (23 and 24), a lacrimal sac (26), a nasolacrimal duct (27), and others. The nunchaku-shaped lacrimal duct tube is inserted into the lacrimal duct.

According to a conventionally and commonly used method for placement of a lacrimal duct tube, it is necessary to fumble for intra-lacrimal duct operations. The bougies in the lacrimal duct tube are blindly operated, and it is thus difficult to correctly insert the tube into a curved or obstructed lacrimal duct. If an operator feels large resistance at insertion of the tube, he/she cannot easily determine whether the resistance results from friction between a wall of an obstructed site in the lacrimal duct and the lacrimal duct tube, or results from the bougie's breaking through the lacrimal duct tube, or results from formation of a temporal path (making a hole in a portion other than the lacrimal duct), or the like, and he/she actually forms a false passage in many cases.

In recent years, to avoid such a situation, there has been increasingly populated an operation of inserting a lacrimal duct tube into a lacrimal duct while visually checking the inside of the lacrimal duct using a lacrimal endoscope, thereby allowing the lacrimal duct tube to be correctly inserted into an obstructed lacrimal duct while checking an insertion position. In addition, as treatments using an endoscope have been performed on increasing occasions, it has been found that there has been a difference in treatment results between the case of correctly placing the lacrimal duct tube in a lacrimal duct and the case of placing the lacrimal duct tube in a temporal path. Thus, there has been re-acknowledged the importance of correctly placing the lacrimal duct tube. As described above, although it has been recognized that operations using a lacrimal endoscope are very effective in insertion of the lacrimal duct tube into a lacrimal duct, lacrimal endoscopes are installed in a limited number of hospitals under the present circumstances, for a reason that the devices are expensive and the like.

In addition, to place the lacrimal duct tube in an easy and correct manner, there have been suggested lacrimal duct tube that have a coating for imparting lubricity to the surface of the tube as an insertion member to reduce resistance at time of insertion and improve insertability (refer to Patent Document 2 and Non-patent Document 1). However, using the coating described in Patent Document 2 or Non-patent Document 1 has not necessarily realized sufficient insertability and the like in practical use under the present circumstances.

Next, the occlusion catheter will be described. The occlusion catheter is a medical catheter for use in, for example, (i) obstruction of a blood vessel in the event of rupture of a thoracic or abdominal aortic aneurysm, (ii) interruption of blood flow for drug administration to an intravascular lesion area, (iii) temporary hemostasis before or during surgery, (iv) various cardiac function tests such as measurement of heartbeat pressure by adjustment of blood flow, (v) balloon occlusion test at which cerebral blood vessels are temporarily obstructed to measure spare ability of cerebral blood flow, and the like (as an example, refer to Patent Document 3). The occlusion catheter includes a long tube, a balloon capable of inflation and contraction in the vicinity of a distal-side end portion, and a hub at a proximal-side end portion. Via the hub, a fluid is injected into the balloon or removed from the balloon to inflate or contract the balloon. By inflating the balloon in a blood vessel, it is possible to obstruct the blood vessel and control a blood flow.

As in the foregoing, the occlusion catheter is inserted into a thoracic aorta, abdominal aorta, cardiac blood vessel, cerebral blood vessel, or the like for treatment or investigation of a lesion area. In that case, the occlusion catheter is inserted from a blood vessel in a thigh, elbow, or wrist such that the balloon is positioned near a lesion area in a heart, brain, or the like. At that time, the operator needs to operate a portion of the catheter outside the body to move the occlusion catheter by a certain distance within the bent blood vessel. However, it is not easy to guide the long tube by in-vitro operations to a desired site within the bent blood vessel. Thus, for improving insertability of the catheter, in general, the long tube is made softer in the axial direction continuously or stepwise with increasing proximity to the distal side or a lubricant layer is provided on the surface of the tube to reduce resistance at time of insertion.

Meanwhile, there has been suggested, as a surface coating with excellent lubricity and durability, a specific coating composition with lubricity in wet conditions to be applied to the surface of a base material of a medical instrument, and a coating method using the coating (refer to Patent Document 4). By using the specific coating composition, it can be expected that the tube is improved in insertability. However, there remains the possibility that the coating partially comes off of the surface when the catheter is placed in a living body for a long period of time or when the catheter is inserted by a certain distance during passage through a bent portion of a blood vessel or the like. Thus, further improvement in durability is expected, for example, for application of the coating to medical instruments such as a lacrimal duct tube that is to be placed in a living body for a long period of time and an occlusion catheter that is to be moved by a certain distance within a bent blood vessel, for example.

CITATION LIST

Patent Literatures

Patent Document 1: Japanese Patent No. 2539325
Patent Document 2: JP-A No. 2011-200601
Patent Document 3: JP-A No. 2001-104485
Patent Document 4: International Publication WO 2008/156132

Non-Patent Literature

Non-Patent Document 1: Hiroo Yabe et al., "The Effectiveness and Clinical Applications of a Hydrophilic Heparinized Polyurethane Lacrimal Stent Tube," Journal of Ophthalmic Surgery, 2008, vol. 21, pp. 237 to 242

SUMMARY OF INVENTION

Technical Problem

An object of the present invention is to provide a medical tube that can be easily inserted into and placed in a portion of a living body such as a curved or obstructed lacrimal duct or a bent blood vessel, for example, and has a lubricant layer more improved in durability than conventional ones.

Solution to Problem

In light of the foregoing issue, the inventors of the subject invention have earnestly conducted studies and found that it is possible to provide a medical tube with a lubricant layer improved in durability that can be easily inserted into a portion of a living body such as a curved or obstructed lacrimal duct or a bent blood vessel, for example, by configuring a medical tube such that an intermediate layer and a lubricant layer composed of specific compositions are sequentially laminated on a surface of the tube, thereby completing the invention of the subject application.

The substance of the present invention is as follows:

[1] A medical tube in which an intermediate layer composed of a composition containing (a), (b), and (c1) listed below and a lubricant layer composed of a composition containing (a), (b), and (c2) listed below are sequentially laminated on a surface of an insertion member to be inserted into a living body:

(a) 1 to 35 weight % of at least one of aromatic diisocyanate, aliphatic diisocyanate, and alicyclic diisocyanate;
(b) 1 to 35 weight % of trifunctional or higher functionality polyol;
(c1) 30 to 98 weight % of polyalkylene glycol and/or monomethoxypolyalkylene glycol; and
(c2) 30 to 98 weight % of polyalkylene glycol (including polyalkylene glycol larger in weight-average molecular weight than polyalkylene glycol in (c1)) and/or monomethoxypolyalkylene glycol (including monomethoxypolyalkylene glycol larger in weight-average molecular weight than monomethoxypolyalkylene glycol in (c1)),
(where each of the glycols in (c1) and (c2) is diol).

[2] The medical tube according to [1], wherein the component (c2) includes 10 to 50 weight % of the component (c1).

[3] The medical tube according to [1] or [2], obtained by coating and drying an intermediate layer coating liquid containing the components (a), (b), and (c1) and a solvent and a lubricant layer coating liquid containing the components (a), (b), and (c2) and a solvent, wherein the concentration of the total amount of the components (a), (b), and (c1) in the intermediate layer coating liquid is equal to or less than the concentration of the total amount of the components (a), (b), and (c2) in the lubricant layer coating liquid.

[4] The medical tube according to [3], wherein the concentration of the total amount of the components (a), (b), and (c1) in the intermediate layer coating liquid is 0.1 to 10 weight %, and the concentration of the total amount of the components (a), (b), and (c2) in the lubricant layer coating liquid is 1.0 to 10 weight %.

[5] The medical tube according to any of Claims 1 to 4, wherein a composition of the intermediate layer contains a pre-polymer formed by pre-reaction of at least part of the components (a), (b), and (c1) and/or a composition of the lubricant layer contains a pre-polymer formed by pre-reaction of at least part of the components (a), (b), (c1), and (c2).

[6] The medical tube according to any of [1] to [5], wherein the composition of the intermediate layer is a reaction product obtained by reaction of the components (a), (b), and (c1) and/or the composition of the lubricant layer is a reaction product obtained by reaction of the components (a), (b), (c1), and (c2).

[7] The medical tube according to any of [1] to [6], wherein a material for the insertion member includes at least one selected from a group consisting of silicon resin, isobutylene block copolymer, thermoplastic polyurethane resin, and polyamide resin.

[8] The medical tube according to any of [1] to [7], wherein the medical tube is a lacrimal duct tube to be inserted into a lacrimal duct and to be placed in the same.

[9] The medical tube according to [8], wherein the material for the insertion member includes a thermoplastic polyurethane resin containing an isobutylene block copolymer.

[10] A production method of the medical tube according to any of [1] to [9], including the steps of preparing an intermediate layer coating liquid containing the components (a), (b), and (c1) and a solvent; and preparing a lubricant layer coating liquid containing the components (a), (b), and (c2) and a solvent, so as to include 10 to 50 weight % of the intermediate layer coating liquid.

[11] The production method of the medical tube according to [9], including the steps of: coating the intermediate layer coating liquid containing the components (a), (b), and (c1) and the solvent to the insertion member; drying the intermediate layer coating liquid; coating the lubricant layer coating liquid in which the concentration of the total amount of the components (a), (b), and (c2) is equal to or larger than the concentration of the total amount of the components (a), (b), and (c1) of the intermediate layer coating liquid; and drying the lubricant layer coating liquid, thereby to laminate in sequence the intermediate layer and the lubricant layer on the surface of the insertion member.

[12] The production method of the medical tube according to [11], wherein the concentration of the total amount of the components (a), (b), and (c1) in the intermediate layer coating liquid is 0.1 to 10 weight %, and the concentration of the total amount of the components (a), (b), and (c2) in the lubricant layer coating liquid is 1.0 to 10 weight %.

[13] The production method of the medical tube according to any of [10] to [12], wherein the step of coating the intermediate layer coating liquid and/or the lubricant layer coating to the placement member is dipping, coating by a sponge including the intermediate layer coating liquid and/or the lubricant layer coating, coating by a brush including the intermediate layer coating liquid and/or the lubricant layer coating, or spraying.

Advantageous Effects of Invention

According to the present invention, the lubricant layer composed of a specific composition provides sufficient lubricity to the surface of the insertion member in wet conditions, and thus the medical tube can be easily inserted into a living body. In addition, the lubricant layer is further improved in durability than conventional ones, and makes it possible to suppress dropping of the lubricant layer from the surface of the insertion member.

In addition, if the medical tube is a lacrimal duct tube, for example, the surface of the lacrimal duct tube is sufficiently lubricant in wet conditions, which makes it possible to reduce friction between a lacrimal duct wall and the tube. In addition, if any force is applied to the tube so as to form a false passage, resistance to the operator's hand becomes large, and thus the formation of a false passage can be recognized from a difference in resistance to the operator's hand. This makes it possible to insert the lacrimal duct tube in an easy and correct manner into a curved or obstructed lacrimal duct and place the same there under no overload and without breaking through the lacrimal duct tube or formation of a false passage. Further, the intermediate layer and the lubricant layer composed of specific compositions are sequentially laminated on the surface of the placement member, and thus the tube is improved in durability and thus is preferably used as a lacrimal duct tube that is supposed to be placed for a long period of time (for example, about two weeks to two months).

Moreover, if the medical tube is a catheter that is inserted into a bent blood vessel or the like, such as an occlusion catheter, for example, the surface of the occlusion catheter is sufficiently lubricant in wet conditions, and thus resistance of contact with a blood vessel wall or the like decreases to improve insertability. In addition, the tube is improved in durability, which makes it possible to suppress dropping of the lubricant layer even if the tube is inserted by a certain distance during passage through a bent portion of the blood vessel.

DESCRIPTION OF EMBODIMENTS

The present invention will be described below in detail.
The present invention is a medical tube in which an intermediate layer composed of a composition containing (a), (b), and (c1) listed below and a lubricant layer composed of a composition containing (a), (b), and (c2) listed below are sequentially laminated on a surface of an insertion member to be placed in a living body. As for (c1) and (c2), each of the glycols is diol.

(a) 1 to 35 weight % of at least one of aromatic diisocyanate, aliphatic diisocyanate, and alicyclic diisocyanate;
(b) 1 to 35 weight % of trifunctional or higher functionality polyol
(c1) 30 to 98 weight % of polyalkylene glycol and/or monomethoxypolyalkylene glycol;
(c2) 30 to 98 weight % of polyalkylene glycol (including polyalkylene glycol larger in weight-average molecular weight than polyalkylene glycol in (c1)) and/or monomethoxypolyalkylene glycol (including monomethoxypolyalkylene glycol larger in weight-average molecular weight than monomethoxypolyalkylene glycol in (c1));

In the following description, the compositions containing (a), (b), and (c1) and/or (c2) may be referred to "coating composition."

In the present invention, as described above, the lubricant layer composed of a composition containing the component (c2) different in weight-average molecular weight from the component (c1) of the intermediate layer is formed on the surface of the intermediate layer, whereby the intermediate layer and the lubricant layer are laminated.

In particular, since the lubricant layer is larger in weight-average molecular weights of polyalkylene glycol and monomethoxypolyalkylene glycol than those of the intermediate layer, the lubricant layer is sufficiently lubricant in wet conditions in the presence of the component (c2). In addition, by using the intermediate layer that is relatively smaller in weight-average molecular weight(s) of polyalkylene glycol and/or monomethoxypolyalkylene glycol, it is possible to improve joint strength with the surface of the insertion member based on the components (a) and (b) while maintaining affinity with the lubricant layer.

As described above, by disposing the intermediate layer composed of a specific composition between the insertion member and the lubricant layer, it is possible to effectively suppress separation of the lubricant layer from the insertion member. Specifically, it is possible to improve joint strength between the lubricant layer formed on the surface of the insertion member and the intermediate layer (hereinafter, the two layers will also be referred to collectively as "coating layer"), and if the medical tube is a lacrimal duct tube, for example, it is possible to obtain a lacrimal duct tube that suppresses separation of the coating layer over a long period of time even if the lacrimal duct tube is placed in a lacrimal duct for a long period of time, thereby obtaining the lacrimal duct tube improved in durability. In addition, when the lacrimal duct tube is inserted into a lacrimal duct, the lubricant layer is sufficiently lubricant in wet conditions, and thus it is possible to reduce friction between the lacrimal duct wall and the tube. Further, when the lacrimal duct tube is blindly inserted into the curved or obstructed lacrimal duct, even if a load is abruptly applied between the lacrimal duct tube and the lacrimal duct wall, it is possible to reduce the possibility of separation of the coating layer because of an improvement in joint strength. Accordingly, even if the lacrimal duct tube is inserted and placed for a long period of time, the coating layer is less prone to separate, and thus the residual coating layer facilitates removal of the lacrimal duct tube after completion of the treatment. In addition, if the medical tube is an occlusion catheter, for example, joint strength between the lubricant layer and the intermediate layer is also improved. Thus, even when the occlusion catheter is inserted into a bent blood vessel, it is possible to suppress dropping of the lubricant layer due to contact between the occlusion catheter and the blood vessel wall or the like because the occlusion catheter is improved in insertability in the presence of the lubricant layer and improved in durability.

In the present invention, the lubricant layer may have a single-layer structure or a multi-layer structure with two or more layers. In either case, the same performance can be expected.

The foregoing component (a) will be described.

The aromatic diisocyanate, aliphatic diisocyanate, and alicyclic diisocyanate for use in (a) are isocyanate compounds that have functional groups with two isocyanate groups in one molecule. The coating composition contains at least one of these diisocyanates.

There is no particular limitation on aromatic diisocyanate as far as advantages of the present invention can be produced. For example, the aromatic diisocyanate may be 2,4-tolylene diisocyanate, 2,6-tolylene diisocyanate, 4,4'-diphenylmethane diisocyanate, p-phenylene diisocyanate, 3,3'-dimethylphenyl 4,4'-diisocyanate, metaxylylene diisocyanate, dianisidine diisocyanate, tetramethylxylene diisocyanate, 1,5-naphthalene diisocyanate, and the like.

There is no particular limitation on aliphatic diisocyanate as far as the advantages of the present invention can be produced. For example, the aliphatic diisocyanate may be trans-vinylene diisocyanate, 2,2,4-trimethylhexamethylene diisocyanate, lysine diisocyanate, 1,6-hexamethylene diisocyanate, and the like.

There is no particular limitation on alicyclic diisocyanate as far as the advantages of the present invention can be produced. For example, the alicyclic diisocyanate may be trans-1,4-cyclohexane diisocyanate, cis-1,4-cyclohexane diisocyanate, 4,4'-dicyclohexylmethane diisocyanate, isophorone diisocyanate, and the like.

In the present invention, one or two or more of the isocyanates can be used in combination.

In the present invention, the content of the foregoing diisocyanate component of the coating composition in the intermediate layer is 1 to 35 weight %, preferably 5 to 30 weight %, and more preferably 10 to 25 weight %. If the content of the diisocyanate component falls below this range, the force of adhesion to the placement member and the durability of the intermediate layer when being subjected to friction decrease in an unfavorable manner. If the content of the diisocyanate component exceeds this range, the intermediate layer becomes friable unfavorably.

The content of the foregoing diisocyanate component of the coating composition in the lubricant layer is 1 to 35 weight %, preferably 3 to 30 weight %, and more preferably 5 to 20 weight %. If the content of the diisocyanate component falls below this range, the force of adhesion to the intermediate layer and the durability of the lubricant layer when being subjected to friction decrease in an unfavorable manner. If the content of the diisocyanate component exceeds this range, the lubricant layer becomes friable unfavorably.

The foregoing component (b) will be described.

The trifunctional or higher functionality polyol for use in (b) is a virtually trifunctional or higher functionality polyol having more hydroxyl groups than two functions. In the present invention, in particular, a trifunctional or higher functionality polyol is an essential component. By containing a trifunctional or higher functionality polyol, it is possible to provide durability of the coating layer, in particular, significantly suppress a rise in friction load when the lubricant layer and the lacrimal duct wall contact each other.

There is no particular limitation on trifunctional or higher functionality polyol as far as the advantages of the present invention can be produced. For example, the trifunctional or higher functionality polyol may be polyether polyols such as polyester polyol, poly(oxypropylene ether) polyol, poly(oxyethylene-propylene ether) polyol, and polytetramethylene glycol, branched derivatives of polymeric polyols such as acrylic polyol, ricinus oil and its derivatives, glycerin, trimethylolpropane, trimethylol ethane, 1,2,6-hexanetriol, pentaerythritol, sorbitol, mannitol, and the like.

In the present invention, the content of the foregoing trifunctional or higher functionality polyol component of the coating composition in the intermediate layer is 1 to 35 weight %, preferably 3 to 25 weight %, and more preferably 5 to 15 weight %. If the content of the trifunctional or higher functionality polyol in the intermediate layer falls below this range, the force of adhesion to the placement member and the durability of the intermediate layer when being subjected to friction decrease in an unfavorable manner. If the content of the trifunctional or higher functionality polyol exceeds this range, the intermediate layer unfavorably becomes sticky and generates tucking.

In the present invention, the content of the foregoing trifunctional or higher functionality polyol component of the coating composition in the lubricant layer is 1 to 35 weight %, preferably 2 to 25 weight %, and more preferably 3 to 15 weight %. If the content of the trifunctional or higher functionality polyol in the lubricant layer falls below this range, the force of adhesion to the intermediate layer and the durability of the lubricant layer when being subjected to friction decrease in an unfavorable manner. If the content of the trifunctional or higher functionality polyol exceeds this range, the lubricant layer unfavorably becomes sticky and generates tucking.

Diisocyanate in the component (a), a trifunctional or higher functionality polyol in the component (b), a specific glycol in the component (c1), and a specific glycol in the component (c2) may be partially reacted in advance and added as urethane polymers or the like. In this case, the proportion of the components (a), (b), (c1), and (c2) is calculated based on the amounts of the components before the reaction. There is no particular limitation on the amounts of the components (b), (c1), and (c2) reacting with the component (a) to form a pre-polymer, provided that the coating composition in the scope of the present invention can be obtained. The pre-polymer is preferably formed from 100 weight % or less of the component (a), 0 to 75 weight % of the component (b), and 0 to 50 weight % of the components (c1) and (c2). The ratio of (a)/(b) is preferably 3/1 to 1/3. If the ratio of the component (b) exceeds this range, the pre-polymer becomes increasingly hardened to reduce reaction between the isocyanate group in the component (a) and the components (c1) and (c2) in an unfavorable manner. If the ratio of the component (b) falls below this range, the reactive pre-polymer unfavorably deteriorates in handling performance. The ratios of (a)/(c1) and (a)/(c2) are preferably in the range of 3/1 to 1/30 by weight. If the amounts of the components (c1) and (c2) exceed this range, the isocyanate group in the component (a) reacting with the component (b) becomes unfavorably smaller to decrease three-dimensional cross-linkage. If the amounts of the components (c1) and (c2) fall below this range, the reactive pre-polymer unfavorably deteriorates in handling performance. Also in the case of adding concurrently the component (a), the component (b), and the components (c1) and (c2) to form a pre-polymer, the foregoing ranges are preferably used.

The foregoing components (c1) and (c2) will be described.

There is no particular limitation on polyalkylene glycols capable of being used in (c1) and (c2) as far as the advantages of the present invention can be produced. For example, such polyalkylene glycols may be polyethylene glycol, polypropylene glycol, and the like.

There is no particular limitation on monomethoxypolyalkylene glycols capable of being used in (c1) and (c2) as far as the advantages of the present invention can be produced. For example, such monomethoxypolyalkylene glycols may be monomethoxypolyethylene glycol, monomethoxypolypropylene glycol, and the like.

In addition, there is no particular limitation on derivatives of the foregoing glycols as far as the advantages of the present invention can be produced. For example, such derivatives may be tripolyethylene glycol ether of glycerin, tetrapolyethylene glycol ether of diglycerine, tetrapolyethylene glycol ether of pentaerythritol, and the like.

In the present invention, the polyalkylene glycols and monomethoxypolyalkylene glycols for use in (c1) and (c2) including the foregoing derivatives, are diols.

In the present invention, there is no particular limitation on weight-average molecular weight(s) of polyalkylene glycol and/or monomethoxypolyalkylene glycol in the component (c1) of the coating composition in the intermediate layer as far as the weight-average molecular weight(s) are smaller than those of the component (c2) in the lubricant layer. The weight-average molecular weight(s) are preferably 500 or more and 50000 or less, more preferably 1000 or more and 40000 or less, and further preferably 2000 or more and 30000 or less. If the weight-average molecular weight(s) exceed the foregoing range, the coating layer tends to decrease in durability. If the weight-average molecular weight(s) fall below the foregoing range, there arises a larger difference in weight-average molecular weight between the intermediate layer and the lubricant layer, and the lubricant layer tends to decrease in durability.

In the present invention, there is no particular limitation on weight-average molecular weight(s) of polyalkylene glycol and/or monomethoxypolyalkylene glycol in the (c2) of the coating composition in the lubricant layer as far as the weight-average molecular weight(s) are larger than those of the component (c1) in the intermediate layer. The weight-average molecular weight(s) are preferably 10000 or more and 60000 or less, more preferably 15000 or more and 50000 or less, and further preferably 20000 or more and 40000 or less. If the weight-average molecular weight(s) fall below the foregoing range, the lubricant layer tends to be low in lubricity in wet conditions. If the weight-average molecular weight(s) exceed the foregoing range, the coating layer tends to decrease in durability.

In the present invention, as described above, the glycols of the (c2) in the lubricant layer include glycols larger in weight-average molecular weight than the glycols of the (c1) in the intermediate layer. In addition, as a relationship between the two layers in weight-average molecular weight, the weight-average molecular weights of the glycols in the lubricant layer are preferably 2 to 12 times larger, more preferably 3 to 10 times larger, further preferably 4 to 8 times larger than the weight-average molecular weights of the glycols in the intermediate layer. This produces a lubricant and durable coating.

In the present invention, the content(s) of polyalkylene glycol and/or monomethoxypolyalkylene glycol in the (c1) of the coating composition in the intermediate layer is/are in the range of 30 to 98 weight %, preferably 40 to 95 weight %, and more preferably 50 to 90 weight %. If the content(s) of polyalkylene glycol and/or monomethoxypolyalkylene glycol fall below this range, the isocyanate groups to react with the polyalkylene glycol and/or monomethoxypolyalkylene glycol tend to decrease. If the same exceeds this range, the coating layer tends to decrease in durability when being subjected to friction.

In the present invention, the content(s) of polyalkylene glycol and/or monomethoxypolyalkylene glycol in the (c2) of the coating composition in the lubricant layer is/are in the range of 30 to 98 weight %, preferably 40 to 95 weight %, and more preferably 50 to 90 weight %. If the content(s) of polyalkylene glycol and/or monomethoxypolyalkylene glycol fall below this range, the lubricant layer tends to decrease in lubricity. If the same exceeds this range, the coating layer tends to decrease in durability when being subjected to friction.

In the present invention, the glycols of the (c2) in the lubricant layer include glycols larger than in weight-average molecular weight than the glycols of the (c1) in the intermediate layer. In addition, all of the glycols in the lubricant layer may be larger in weight-average molecular weight than those in the intermediate layer, or may be equal to or less than in weight-average molecular weight than those in the intermediate layer.

In the latter case, for example, the polyalkylene glycol and/or monomethoxypolyalkylene glycol of the (c2) in the lubricant layer may be configured to include preferably 10 to 50 weight %, more preferably 15 to 45 weight %, and further preferably 20 to 40 weight % of that (those) of the (c1) in the intermediate layer. This makes it possible to maintain durability of the intermediate layer and the lubricant layer.

In the present invention, to form the intermediate layer and the lubricant layer on the surface of the insertion member, an intermediate layer coating liquid and a lubricant layer coating liquid are prepared. In addition, as a relationship between the concentration of the total amount of the foregoing (a), (b), and (c1) in the intermediate layer coating liquid and the concentration of the total amount of the components (a), (b), and (c2) in the lubricant layer coating liquid, that is, as a relationship in concentration of coating composition, the concentration of the intermediate layer coating liquid is preferably equal to or less than the concentration of the lubricant layer coating liquid. Accordingly, it is possible to secure film thickness of the finally formed lubricant layer to maintain sufficient lubricity, and reduce film thickness of the intermediate layer to secure joint strength between the lubricant layer and the surface of the placement member.

There is no particular limitation on concentrations of coating compositions in the coating liquids, provided that the foregoing relationship can be maintained. The concentration of the intermediate layer coating liquid is preferably in the range of 0.1 to 10 weight %, more preferably 0.15 to 9.0 weight %, and further preferably 0.2 to 8.0 weight %. The concentration of the lubricant layer coating liquid is preferably in the range of 1.0 to 10 weight %, more preferably 1.1 to 9.0 weight %, and further preferably 1.2 to 8.0 weight %. However, since the lacrimal duct tube is supposed to be placed for a long period of time, the lower concentrations are desired. Thus, the concentration of the intermediate layer coating liquid is preferably in the rage of 0.20 to 5.0 weight %, more preferably 0.60 to 4.0 weight %, and further preferably 0.70 to 3.0 weight %. The concentration of the lubricant layer coating liquid is preferably in the range of 1.0 to 10 weight %, more preferably 1.1 to 9.0 weight %, and further preferably 1.2 to 8.0 weight %. By setting the concentrations of the coating liquids within the foregoing concentration ranges while holding the foregoing concentration relationship, it is possible to keep durability of the intermediate layer and the lubricant layer and lubricity of the lubricant layer.

Materials for the insertion member constituting the medical tube in the present invention will be described. The insertion member refers to a member that constitutes not only a portion to be inserted into a living body and placed there if necessary but also a portion not to be placed within a living body but to contact a living body or a liquid originated from the living body.

Materials for the insertion member usable in the present invention may be any general material usable for a medical tube. For example, the materials may be a polyolefin resin, a polyurethane resin, a polyamide resin, a silicon resin, a polyester resin, an isobutylene copolymer, a polycarbonate, a polyvinyl chloride, and a resin composition including an alloy of the foregoing materials.

Taking as an example the case where the medical tube in the present invention is a lacrimal duct tube, materials for the insertion member constituting the lacrimal duct tube will be described. In the following description, the insertion member constituting the lacrimal duct tube will be referred to as "placement member." In addition, the materials described below can be used not only for a lacrimal duct tube but also for any medical tube according to the use of the tube. In the lacrimal duct tube, the placement member refers to all of members constituting the lacrimal duct tube described later. In the case of a nunchaku-shaped lacrimal duct tube described later, for example, the placement member includes a cylindrical or rod-shaped central part and cylindrical members connected to both ends of the central part.

There is no particular limitation on materials for the placement member for use in the lacrimal duct tube of the present invention. For example, the materials may be a silicon resin, a polyurethane, a polyurethane resin, an isobutylene copolymer, and a resin composition including an alloy of the foregoing materials.

In the present invention, resin compositions including an alloy of isobutylene copolymer and polyurethane resin can be used in a suitable manner. Among them, a resin composition using isobutylene block copolymer as an isobutylene copolymer and a thermoplastic polyurethane resin as a polyurethane resin can be preferably used.

In the case of a resin composed of an isobutylene block copolymer (A) and a thermoplastic polyurethane resin (B), hardness of the placement member (hereinafter, also referred to as simply "tube") can be adjusted by regulating the ratio between the isobutylene block copolymer (A) and the thermoplastic polyurethane resin (B). For example, the hardness of the tube can be made larger by setting larger the ratio of the thermoplastic polyurethane resin (B).

As in the foregoing, the mixture ratio between the (A) and (B) can be set as appropriate. From the viewpoint of antithrombogenicity, surface slidability, and flexibility, the tube preferably includes 1 weight % or more of the isobutylene copolymer (A) (that is, the ratio between the isobutylene block copolymer (A) and the thermoplastic polyurethane resin (B) is (A)/(B)=1/99 or more by weight). From the viewpoint of wear resistance, the ratio between the isobutylene block copolymer (A) and the thermoplastic polyurethane resin (B) is preferably (A)/(B)=1/99 to 70/30 by weight. From the viewpoint of compression stress, the ratio between the isobutylene block copolymer (A) and the thermoplastic polyurethane resin (B) is preferably (A)/(B)=1/99 to 50/50 by weight.

In the present invention, the material for use in the placement member may be composed of only the isobutylene block copolymer (A) and the thermoplastic polyurethane resin (B). Alternatively, medicinal properties, blood anticoagulant, disintegrants, absorption promoters of medicinal properties, plasticizer, stabilizer, radiation absorbent, and if desired, various compounding components that are generally used in the relevant field such as polymer compounds other than the foregoing ones may be used for the placement member.

Preferred as the isobutylene block copolymer (A) is "SIBSTAR (registered trademark) 102T" produced by Kaneka Corporation, which is a styrene-isobutylene-styrene block copolymer (hereinafter, also referred to as SIBS). However, the (A) is not limited to this.

Preferred as the thermoplastic polyurethane resin (B) are "Miractran E385PNAT" produced by Nippon Miractran Co., Ltd. and "Tekotan TT1074A" produced by Lubrizol Corporation, which are ether aromatic cyclic polyurethanes, or "Tecoflex EG100A" and "Tecoflex EG85A" produced by Lubrizol Corporation, which are ether cycloaliphatic polyurethanes, or "Karubotan PC3575A" produced by Lubrizol Corporation, which is a polycarbonate polyurethane. However, the (B) is not limited to them.

In the present invention, by employing the intermediate layer formed from a specific coating composition, the joint strength of the coating layer to the placement member is improved. From the viewpoint of further improving joint strength between the placement member and the intermediate layer, the functional groups of the components contained in the coating composition of the intermediate layer and the functional groups contained in the material for the placement member constituting the lacrimal duct tube preferably have common portions. This improves affinity between the surface of the placement member and the intermediate layer, thus enhances joint strength between the two, and eventually enhances durability of the coating layer. In addition, from this viewpoint, the functional groups contained in the coating composition of the intermediate layer and the functional groups contained in the material constituting the placement member are more preferably identical. Such functional groups may be obtained by combining as appropriate the foregoing coating composition and the material constituting the placement member. The combination may be a carboxyl group, a group containing amide bond, a group containing urethane bond, and the like, for example. Among them, from the viewpoint of hydrogen bonding, a carboxyl group is preferred, a group containing amide bond is more preferred, and a group containing urethane bond is further preferred. In addition, the relationship between the coating composition in the intermediate layer and the functional groups contained in the placement member applies to not only a lacrimal duct tube but also other medical tubes such as an occlusion catheter described later, and the like.

One embodiment of a structure of the lacrimal duct tube in the present invention will be briefly described below. Prior to the description of the lacrimal duct tube, a lacrimal duct in which the lacrimal duct tube of the present invention is inserted and placed will be briefly described with reference to the drawing. FIG. 2 shows schematically an anatomical structure of a lacrimal duct. The lacrimal duct is a duct (ocular adnexa) composed of upper/lower lacrimal punctum (21/22), upper/lower lacrimal canaliculus (23/24), a common canaliculus (25), a lacrimal sac (26), a nasolacrimal duct (27), a nasal cavity (not shown), and Hasner's valve (not shown), as shown in FIG. 2, and configured to guide a lacrimal fluid produced by a lacrimal gland (not shown) from an eye surface to an inferior nasal meatus (28). In addition, a duct extending from the upper lacrimal punctum (21) through the upper lacrimal canaliculus (23) and the common canaliculus (25) to the inferior nasal meatus (28) is referred to as an upper lacrimal duct, and a duct extending from the lower lacrimal punctum (22) through the lower lacrimal canaliculus (24) and the common canaliculus (25) to the inferior nasal meatus (28) is referred to as a lower lacrimal duct.

There is no particular limitation on structure of the lacrimal duct tube in the present invention as far as the tube can be inserted and placed in the lacrimal duct as described above. For example, the present invention may be a so-called nunchaku-shaped lacrimal duct tube as described above. The nunchaku-shaped lacrimal duct tube will be briefly described with reference to the drawing.

Figure 1:
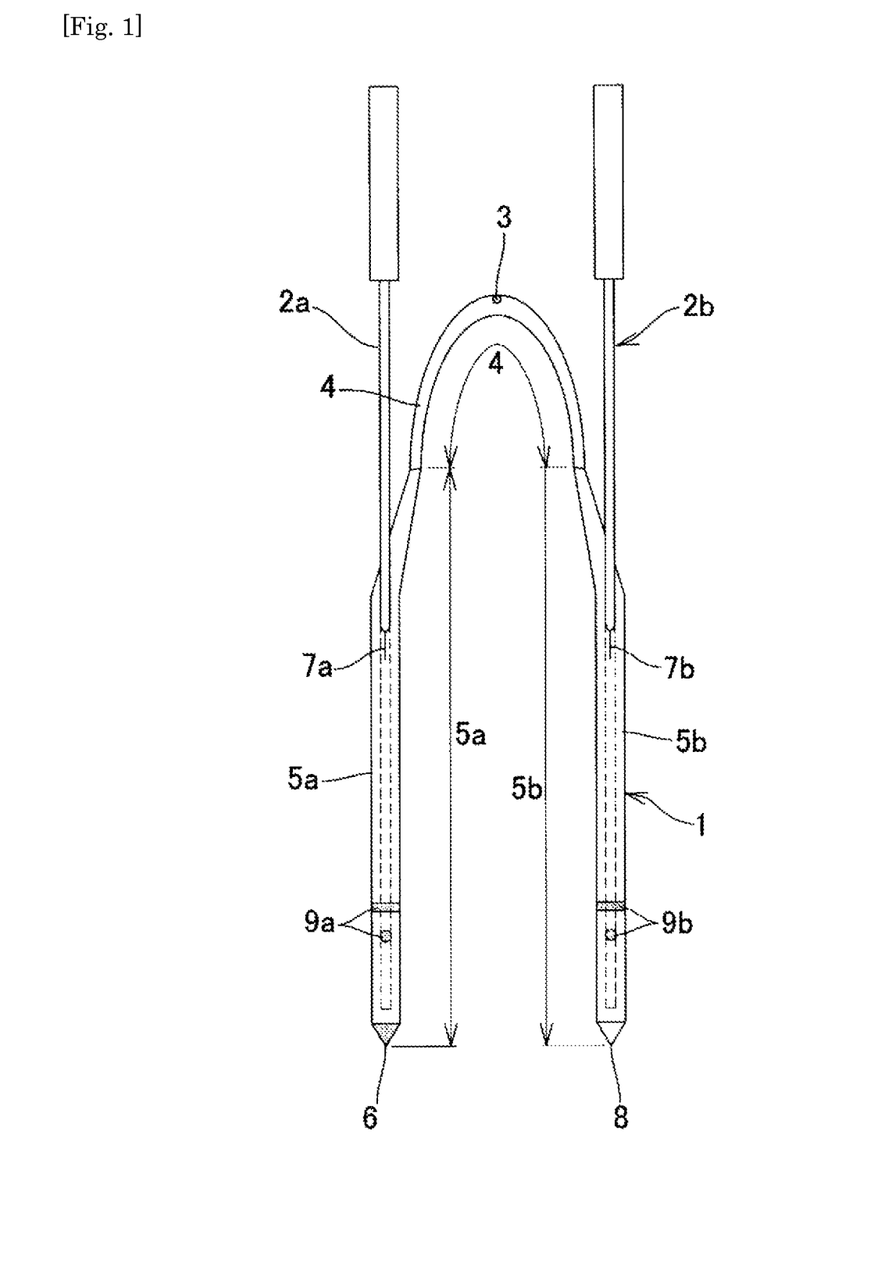
FIG. 1 is a diagram showing a lacrimal duct tube.

FIG. 1 shows one example of a nunchaku-shaped lacrimal duct tube 1 (in which bougies are inserted). The nunchaku-shaped lacrimal duct tube 1 includes: a cylindrical or rod-shaped central part 4 that is placed in lacrimal punctum, lacrimal canaliculus, common canaliculus, and lacrimal sac; a first cylindrical part 5a that is connected to one end of the central part 4 and is placed in a lacrimal sac, nasolacrimal duct, Hasner's valve, and inferior nasal meatus; and a second cylindrical part 5b that is connected to the other end of the central part 4 and is placed in a lacrimal sac, nasolacrimal duct, Hasner's valve, and inferior nasal meatus. The central part 4 has a so-called nunchaku shape that is made thinner than the first cylindrical part 5a and the second cylindrical part 5b.

In this example, a first terminal end 6 of the first cylindrical part 5a and a second terminal end 8 of the second cylindrical part 5b are blind ends and have pointed tips. The terminal ends of the cylindrical parts may be opened to check the inside of the lacrimal duct using an endoscope. The tip end portion including the first terminal end 6 is colored to allow an operator to easily discriminate from the tip end portion including the second terminal end 8. In addition, two marks 9a are given to the first cylindrical part 5a at predetermined positions from the first terminal end 6, which allows an operator to visually check the depth of insertion. Similarly, marks 9b are given to the second cylindrical part 5b.

The first cylindrical part 5a and the second cylindrical part 5b have on side walls cuts 7a and 7b for insertion of bougies, respectively, in the vicinity of the central part 4. Through the cuts 7b and cuts 7a, a first bougie 2a and a second bougie 2b are inserted into hollow portions of the first cylindrical part 5a and the second cylindrical part 5b, respectively. The central part 4 has a middle point mark 3 in an almost middle of the nunchaku-shaped lacrimal duct tube 1 to facilitate verification of an insertion position and a placement position.

Further, the foregoing coating layer (not shown) is formed on the surface of the first cylindrical part 5a, the second cylindrical part 5b, and, if necessary, the central part 4.

Taking as an example the case where the medical tube of the present invention is an occlusion catheter, the material for the insertion member constituting the occlusion catheter will be described.

The insertion member in the occlusion catheter is inserted into a blood vessel and contacts a blood vessel wall and the like. In the embodiment described later, the insertion member is a base material for an inner tube (in particular, a distal-side end portion), an outer tube, and a balloon.

There is no particular limitation on materials for the insertion member for use in the occlusion catheter. For example, the materials may be one or two or more of synthetic resins including polyolefin resins such as polyolefin and polyolefin elastomer, polyurethane resins such as polyurethane and polyurethane elastomer, polyamide resins such as polyamide and polyamide elastomer, polyester resins such as a polyethylene terephthalate, silicon resins, and styrene resins such as styrene elastomer. In addition, these materials can be selected as appropriate according to the use of the insertion member.

In the case of configuring the base material for the inner tube and the outer tube in a multi-layer structure, it is preferred to arrange a layer including these synthetic resins on the surface of the insertion member so as to contact the intermediate layer. In addition, in the case of configuring the multi-layer structure as described above, a reinforcement layer may be provided to reinforce the inner tube and/or the outer tube. Materials for the reinforcement layer may be, for example, various metals including stainless steel, tungsten, alloy of C—Mn—Si—P—S—Cr—Mo—Ni—Fe—X (X=Au, Os, Pd, Re, Ta, Ir, or Ru), alloy of C—Mn—Si—P—S—Cr—Mo—Ni—X (X=Au, Os, Pd, Re, Ta, Ir, or Ru), copper, nickel, titanium, piano wire, Co—Cr alloy, Ni—Ti alloy, Ni—Ti—Co alloy, Ni—Al alloy, Cu—Zn alloy, Cu—Zn—X alloy (e.g. X=Be, Si, Sn, Al, or Ga), amorphous alloy, and others. Further, an inner layer may be provided on the inside of the inner tube to improve insertability of the guide wire. Materials for the inner layer are preferably lubricant materials, and may be synthetic resins including fluorine resins such as polytetrafluoroethylene, polyolefin resins such as polyethylene, and the like, for example.

Further, a plurality of resins different in hardness may be axially arranged on the occlusion catheter to change hardness of the inner tube and/or the outer tube in the axial direction.

One embodiment of a structure of an occlusion catheter will be briefly described with reference to the drawings.

Figure 3:
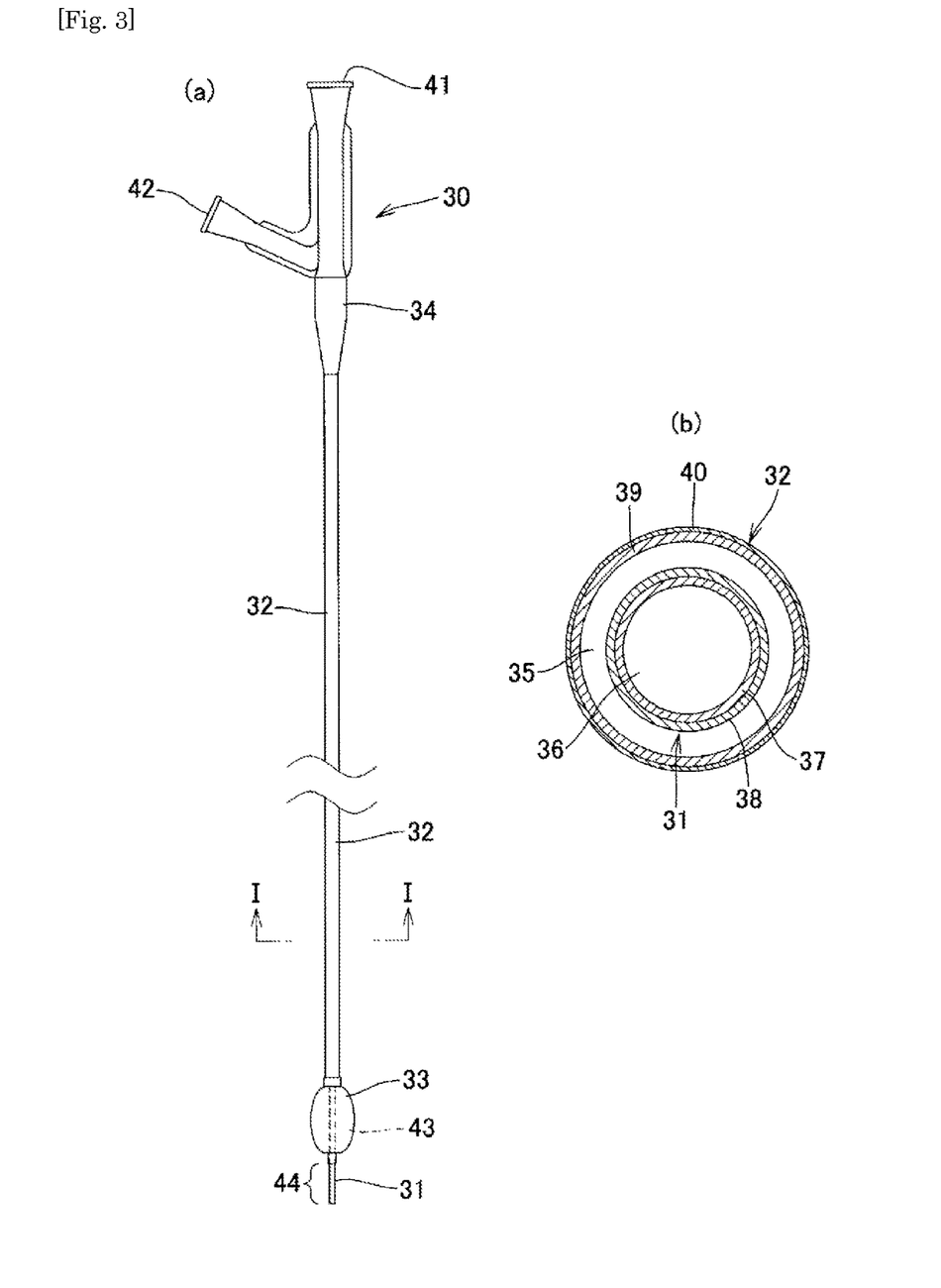
FIG. 3(a) is a diagram showing an occlusion catheter.
FIG. 3(b) is a diagram showing an I-I cross section of FIG. 3(a).

FIG. 3(a) is a schematic diagram showing an occlusion catheter 30, and FIG. 3(b) is a schematic diagram showing an I-I cross section of FIG. 3(a). As illustrated in FIG. 3, the occlusion catheter in the embodiment includes a long tube formed by an inner tube 31 and an outer tube 32, a balloon 33, and a hub 34.

The balloon 33 has a cylindrical structure, and the inner tube 31 penetrates through the inside of the cylindrical shape. In addition, a distal-side end portion of the balloon 33 is joined to the vicinity of a distal-side end portion of the inner tube 31. A proximal-side end portion of the balloon 33 is joined to a distal-side end portion of the outer tube 32.

The inner tube 31 is opened at the distal end and the proximal end, and includes a luminal part 36 that communicates from the distal end to the proximal end. The inner tube 31 is used for insertion of a guide wire, injection of a drug solution, discharge of a body fluid, and the like.

The outer tube 32 is opened at the distal end and the proximal end, and includes a luminal part that communicates from the distal end to the proximal end. In addition, by arranging the inner tube 31 in the luminal part, a portion formed by an outer peripheral surface of the inner tube 31 and an inner peripheral surface of the outer tube 32 is formed (shown with reference numeral 35 in FIG. 3(*b*)). This portion functions as a balloon lumen 35 that lets through a fluid for inflating the balloon 33.

The hub 34 includes a first opening part 41 that communicates with the luminal part 36 of the inner tube 31 and is used for insertion of a guide wire, injection of a drug solution, and the like. The hub 34 also includes a second opening part 42 that communicates with the balloon lumen 35 and is used to inject or remove the balloon fluid for inflating the balloon 33.

As illustrated in FIG. 3(*b*), in the embodiment, the base material for the inner tube 31 has a two-layer structure of an inner layer 37 and a second layer 38. Materials for the inner layer 37 are preferably selected as materials for improving insertability of a guide wire as described above. Materials for the outer layer 38 may be the foregoing various resins. If necessary, to change hardness of the outer layer 38 in the axial direction, a plurality of resins different in hardness may be arranged such that hardness becomes gradually larger from the distal end to the proximal end. In addition, a reinforcement layer may be further provided between the inner layer 37 and the outer layer 38.

In addition, although not illustrated, to check the position of the distal-side end portion of the occlusion catheter 30 and the position of the balloon 33 by X-ray illumination, radiopaque markers may be provided on the distal-side end portion of the base material of the inner tube 31 and a portion of the balloon 33 where the luminal part 43 is arranged. The radiopaque markers may be made of publicly-known metallic materials.

Further, a coating layer is provided to the distal-side end portion of the inner tube 31 at a portion 44 not covered by the balloon 33 and the outer tube 32.

Base material 39 for the outer tube 32 is a single layer in the embodiment, but may be configured in a multi-layer structure as with the base material for the inner tube 31, or may be provided with a reinforcement layer. In addition, hardness of the base material 39 may be changed in the axial direction as with the base material for the inner tube 31. Further, the base material 39 may be larger in outer diameter in the axial direction with increasing proximity to the proximal side.

Formed on an outer peripheral surface of the base material 39 is a coating layer 40 in which the foregoing specific intermediate layer and lubricant layer are sequentially laminated.

Base material for the balloon 33 may have a single-layer or multi-layer structure of a cross section that is orthogonal to the axial direction of the occlusion catheter 30. In addition, the balloon 33 is preferably a compliant balloon that changes in outer diameter according to the amount of injection of a fluid to the luminal part 43 of the balloon 33. Therefore, a material for the base material of the balloon 33 is preferably a soft material, for example, polyurethane elastomer, silicon resin, polyamide resin, or the like. Formed on the outer peripheral surface of the base material for the balloon 33 is a coating layer in which the foregoing specific intermediate layer and lubricant layer are sequentially laminated.

In the foregoing detailed description, the medical tube in the present invention is a lacrimal duct tube or an occlusion catheter as an example. However, the present invention is not limited to these examples, but the foregoing coating layer can also be applied to various medical tubes.

An embodiment of a production method of a medical tube in the present invention will be briefly described.

In one embodiment of the production method according to the present invention, first, a medical tube including an insertion member having a desired structure is fabricated. If the medical tube is to be a lacrimal duct tube, a lacrimal duct tube having the structure illustrated in FIG. 1 (excluding the coating layer), for example, is fabricated. If the medical tube is to be an occlusion catheter, an occlusion catheter having the structure illustrated in FIG. 3 (excluding the coating layer), for example, is fabricated. Next, an intermediate layer and a lubricant layer are sequentially laminated on the surface of the insertion member in the medical tube, thereby obtaining the medical tube.

In another embodiment, at the stage of fabricating constitutional members of the medical tube, an intermediate layer and a lubricant layer may be sequentially formed on the surfaces of the members, and then the members may be assembled into the medical tube. For example, in the case of the lacrimal duct catheter illustrated in FIG. 1, at the stages of producing the first cylindrical part 5*a*, the second cylindrical part 5*b*, and the central part 4, an intermediate layer and a lubricant layer may be sequentially formed, and after that, these parts may be assembled to produce the lacrimal duct tube 1. By producing the tube in this manner, it is possible to produce large numbers of the first and second cylindrical parts and the central part in advance to enhance production efficiency of the lacrimal duct tube. In addition, in the case of producing the occlusion catheter 30 illustrated in FIG. 3, for example, at the stage of fabricating the constitutional members as in the same manner as described above, an intermediate layer and a lubricant layer may be sequentially formed on surfaces of members to be in contact with a living body (for example, tip end portions of the outer tube 32, the balloon 33, and the inner tube 31 illustrated in FIG. 3), and after that, the members may be assembled into the occlusion catheter 30.

There is no particular limitation on formation method of the intermediate layer and the lubricant layer. For example, an intermediate layer coating liquid is prepared by mixing a coating composition including the foregoing components (a), (b), and (c1) with a solvent, and a lubricant layer coating liquid is prepared by mixing a coating composition including the foregoing components (a), (b), and (c2) (if necessary, also the component (c1)) with a solvent, and the intermediate layer coating liquid is applied to the surface of the insertion member and dried, and the lubricant layer coating liquid is applied to the same surface and dried, thereby to form a coating layer in which the intermediate layer and the lubricant layer are sequentially laminated on the surface of the insertion member.

In the present invention, at formation of the coating layer, the intermediate layer coating liquid and the lubricant layer coating liquid are prepared. At that time, the lubricant layer coating liquid may be prepared so as to include 10 to 50 weight % of the intermediate layer coating liquid. In addition, the intermediate layer coating liquid with predetermined concentration of the coating composition, and the lubricant layer coating liquid with the concentration of the coating composition larger than the concentration of the coating composition in the intermediate layer coating liquid, may be prepared, and these liquids may be used to form a desired coating layer. In this case, the concentration of the coating composition in the intermediate layer coating liquid may be 0.1 to 10.0 weight %, and the concentration of the coating composition in the lubricant layer coating liquid may be 1.0 to 10 weight %.

There is no particular limitation on methods of coating the coating liquids to the surface of the insertion member. For example, conceivable methods of coating the coating liquids include: bringing the coating liquids into contact with the surface of the insertion member to absorb the coating composition into the surface of the insertion member: instilling the coating liquids into a sponge or a brush and moving the sponge or the brush on the insertion member along its length, for example; spraying the coating liquids onto the surface of the insertion member; and dipping the coating liquids, and the like. However, methods of coating the coating liquids are not limited to the foregoing ones.

There is no particular limitation on solvents for use in preparation of the coating liquids. For example, preferred is a non-aqueous solvent that has no active hydrogen to prevent time deterioration of the polyurethane resin produced by reaction between the component (a) and the component (b), has a moderate affinity with the surface of the insertion member, and represents a soluble parameter value $\delta$ of 8 to 13 $[(cal/cm)^{1/2}]$. More preferably, the solvent is a non-aqueous solvent with a soluble parameter value $\delta$ of 9 to 12. In addition, from the viewpoint of uniformity of the coating layer and ease of removing the solvent, a volatile non-aqueous solvent, in particular, an organic solvent is preferably used. Such a solvent may be halogenated hydrocarbons such as acetonitrile, tetrahydrofuran (THF), acetone, ethyl acetate, dichloromethane, and chloroform, for example. THF and acetone are non-aqueous solvents with a soluble parameter value $\delta$ of 9 to 12, for example.

In the present invention, if a reaction product is obtained by reaction of the coating compositions of the intermediate layer and/or the lubricant layer, there is no particular limitation on order of addition or order of reaction. The reaction production may be obtained by reacting in advance at least some of the components (a), (b), (c1), and (c2) to form pre-polymers and then reacting the pre-polymers with the unreacted components (a), (b), (c1), and (c2), or the reaction product may be obtained by reacting mixture of the unreacted components (a), (b), (c1), and (c2). From the viewpoint of availability of raw materials, in particular, the reaction product is preferably produced by blending and reacting the polyalkylene glycol and/or monomethoxypolyalkylene glycol in the components (c1) and (c2) with the diisocyanates in the components (a) and a reaction product of trifunctional or higher functionality polyols in the component (b). There is commercially available a material formed by adding a small amount of the component (b) to the component (a), which is preferably used.

Meanwhile, if reaction is insufficient at that time, an isocyanate group remains in the formed coating layer, and thus there is a fear that adhesion or sticking may occur between coated surfaces or between the coated lacrimal duct tube and a package or a protective member. There is no particular limitation on method for blending and reacting polyalkylene glycol and/or monomethoxypolyalkylene glycol in the components (c1) and (c2) with the diisocyanates in the component (a) and trifunctional or higher functionality polyols in the component (b), provided that a desired reaction product can be obtained. However, from the viewpoints of reduction of insufficient reaction, appropriate reaction speed, and uniform dispersion of compositions, reaction in a solution is used preferably in particular. Preferred as a solvent for use in the reaction is an organic solvent without active hydrogen reactive with isocyanate groups. Such a solvent is preferably a non-aqueous solvent with a predetermined soluble parameter value $\delta$ of 8 to 13 $[(cal/cm)^{1/2}]$ as described above.

Use of water as an active hydrogen compound is not preferred because an insoluble urea may be formed or foam may be generated by formation of urea bond or the like, which deteriorates stability or lubricity of a solution.

The thus obtained medical tube in which the intermediate layer of a specific composition and the lubricant layer exhibiting lubricity in wet conditions are sequentially laminated on the surface of the insertion member, has favorable lubricity and insertability in wet conditions, and is further improved in durability of the coating layer. The medical tube can be used suitably in particular in the case of placing the medical tube in a living body for a long period of time, or moving the medical tube by a certain distance in a portion of a living body such as a bent blood vessel.

EXAMPLES

Examples of the present invention will be described below, but the present invention is not limited to these examples.
[Initial Characteristics]
(1) Measurement of Friction Load Insertion members (tubes) with the coating layers were produced as examples and comparative examples. These insertion members were tested at a friction tester manufactured by HEIDON (Shinto Scientific Co., Ltd.) (model number: TYPE-14DR) at a speed of 5 [mm/sec], with a stroke of 20 [mm], using a hard vinyl chloride friction block with a diameter of 10 [mm]. The test was performed by putting the insertion member into RO water and sliding the insertion member under a load of 100 [gf](1[N]), measuring a friction load after 20 to 1000 reciprocations, and then evaluating the insertion member in lubricity. The load value was determined by measuring the maximum load values at 40 to 60 reciprocations and averaging these measurement values. Evaluation criteria are as follows:

○ (Good): Friction load was equal to or less than 10 gf (0.1N)

× (Not good): Friction load was larger than 10 gf (0.1N)
(2) Outer Appearance

The insertion members (tubes) with the coating layers as examples and comparative examples were tested by dissolving in water evansblue that does not dye the base material of the coating layer surface but dyes the coating composition of the same, coating 1 weight % of the solution to the coating layer surface, and then visually observing the state of the coating layer. Evaluation criteria are as follows:

○ (Good): Immediately after application of the coating, no unevenness of the coating composition was found × (Not good): Immediately after application of the coating, unevenness of the coating composition was found
[Durability]
<1> Durability with Long-Period Placement The tubes with the coating layers as examples and comparative examples were soaked in saline at 37° C., and taken out of the saline one week later, and then subjected to (1)

measurement of friction load and (2) observation of outer appearance. Evaluation methods and criteria are as follows:
(1) Measurement of Friction Load The tubes were measured in the same manner as that in (1) of [Initial characteristics], and evaluated under the same criteria as those in (1) of [Initial characteristics].
(2) Observation of Outer Appearance The tubes were visually observed in state of the coating layer as in the same manner as in (2) of [Initial characteristics]. Evaluation criteria are as follows:

○ (Good): No separation of the coating composition was found x (Not good): Separation of the coating composition was found <2> Friction Resistance (Transition of Friction Load)

The tubes were measured in the same manner as in (1) of [Initial characteristics], and the ratio of the load value after 100 and 1000 reciprocations to the load vale after 2 reciprocations was calculated.

Example 1

Production of Coating Liquids (1) Preparation of Liquid A
The following substance was put into a 10 L reactor.

| 4,4'-diphenylmethane diisocyanate | 6.0 [kg] |

The substance was heated up to 70° C. while being stirred in a nitrogen stream. Then, the following substance was continuously dripped into the former substance over two hours while the former substance was further stirred.

| Ricinus oil | 3.2 [kg] |

The substance was further continuously stirred at 70° C. in a nitrogen stream for two hours, thereby obtaining a polyurethane pre-polymer.
(2) Preparation of Liquid B The liquid A was blended 4.8 g with 1.2 g of ricinus oil and 34 g of THF, and well stirred to obtain liquid B.
(3) Preparation of Liquid C The liquid B was blended 5 g with 25 g of a solution with 10 weight % of THF in polyethylene glycol 4000 (PEG4000), and stirred at 40° C. for three hours, thereby obtaining liquid C. The concentration of components other than THF (coating composition) in the obtained liquid C was 10.8 weight %. The thus obtained liquid was designated as liquid C (1).

Then, a portion of the liquid C (1) was blended with THF for four-fold dilution, thereby obtaining liquid C (1/4) in which the concentration of the coating composition was 2.7 weight %. In addition, a portion of the liquid C (1) was blended with THF for eight-fold dilution, thereby obtaining liquid C (1/8) in which the concentration of the coating composition was 1.4 weight %.
(4) Preparation of Liquid D The liquid B was blended 1.25 g with 25 g of a solution with 10 weight % of THF in polyethylene glycol 35000 (PEG35000), and stirred at 40° C. for three hours, thereby obtaining liquid D. The concentration of components other than THF (coating composition) in the obtained liquid D was 10.2 weight %. The thus obtained liquid was designated as liquid D (1).

Then, a portion of the liquid D (1) was blended with THF for four-fold dilution, thereby obtaining liquid D (1/4) in which the concentration of the coating composition was 2.6 weight %.
(5) Preparation of Liquid E The liquid C and the liquid D prepared in (3) and (4) at the same dilution rate of the coating composition were mixed together at a ratio of 1:2 (by weight), thereby obtaining liquid E. The liquid C (1/4) and the liquid D (1/4) were mixed together at the same ratio, thereby obtaining liquid E (1/4).

Of the foregoing liquids (1) to (5), the composites/composition ratios of the coating compositions in the liquid C (1) and the liquid D (1), and the composition ratio of the liquid E are provided in Table 1.
<Formation of an Intermediate Layer and a Lubricant Layer by Sponge Application>

A resin composition with the weight ratio 90/10 between ether alicyclic polyurethane (Tecoflex EG85A produced by Lubrizol Corporation) and SIBS (SIBSTAR102T produced by Kaneka Corporation) was used to produce an insertion member (tube) with an outer diameter of 1.0 mm and an inner diameter of 0.5 mm.

A sponge (urethane sponge E-16 (white) 25 mm long, 25 mm wide, and 25 mm deep produced by Mafune Engineering Ltd.) was soaked in the liquid C (1/8) obtained in (3) as an intermediate layer coating liquid. The tube was held from four directions and the sponge was moved over the tube in parallel to the length of the tube by a predetermined distance, thereby to coating the liquid C (1/8) to the surface of the tube. After that, the tube was dried at 40° C. for six minutes to form an intermediate layer on the surface of the tube.

Then, a sponge was soaked in the liquid E (1/4) obtained in (5) as a lubricant layer coating liquid. The tube with the intermediate layer was held from four directions and the sponge was moved over the tube in parallel to the length of the tube, thereby to coat the liquid E (1/4) to the tube. After that, the tube was dried at 40° C. for six minutes to obtain the tube in which the intermediate layer and the lubricant layer were sequentially laminated on the surface of the tube.

The obtained tube was subjected to the foregoing evaluation tests. Table 2 shows evaluation results.

Example 2

Production of Coating Liquids

In the same manners as in (1) to (5) of example 1, liquid A, liquid B, liquid C (1), liquid C (1/4), liquid C (1/8), liquid D (1), liquid D (1/4), and liquid E (1/4) were prepared.

In addition, as in the same manner as in (3) of example 1, a portion of the liquid C (1) was blended with THF for 16-fold dilution to prepare liquid C (1/16) in which the concentration of the coating composition was 0.57 weight %, and the same operation was performed for 32-fold dilution to prepare liquid C (1/32) in which the concentration of the coating composition was 0.29 weight %.
<Formation of Coating Layers by Sponge Application>

As indicated in Table 4, the liquid C (1/32), liquid C (1/16), and liquid C (1/8) were used as intermediate layer coating liquids, and the liquid E (1/4) was used as a lubricant layer coating liquid to obtain a tube in which an intermediate layer and a lubricant layer were sequentially laminated on the surface of the tube, in the same manner as in example 1. The obtained tubes were subjected to the foregoing evaluation tests. Table 4 shows evaluation results.

Example 3

Production of Coating Liquids

In the same manners as in (1) to (4) of example 1, liquid A, liquid B, liquid C (1), liquid C (1/2), liquid D (1), and liquid D (1/2) were prepared. The same amounts of the liquid C (1/2) and D (1/2) with the same dilution ratio of the coating composition were mixed together and stirred at 40° C. for one hour, thereby obtaining liquid H (1/2). Table 1 shows the composition ratio of the liquid H.

<Formation of Coating Layers by Dipping>

A tube with an outer diameter of 1.0 mm and a length of 200 mm produced by Pebax was used.

The tube was dipped in the liquid C (1/2) as an intermediate layer coating liquid, and was pulled out in parallel to the length of the tube at a constant speed of 10 mm/sec, thereby to coat the liquid C (1/2) to the surface of the tube. After that, the tube was dried for one hour at room temperature to form an intermediate layer on the surface of the tube.

The tube was dipped in the liquid H (1/2) as a lubricant layer coating liquid, and was pulled out in parallel to the length of the tube at a constant speed of 10 mm/sec, thereby to coat the liquid H (1/2) to the surface of the tube. After that, the tube was dried for one hour at room temperature to obtain the tube in which the intermediate layer and the lubricant layer were sequentially laminated on the surface of the tube.

The obtained tube was subjected to the foregoing evaluation tests. Table 3 shows evaluation results.

Comparative Example 1

Production of a Coating Liquid (1) Preparation of Liquid F

Liquid A was prepared in the same manner as in example 1.

The liquid A was blended 1.2 g with 0.3 g of ricinus oil and 8.5 g of THF, and was well stirred. Next, the liquid A was blended with 80.1 g of a solution with 10 weight % of THF in polyethylene glycol 20000 (PEG20000), and stirred at 40° C. for three hours, thereby obtaining liquid F.

<Formation of Lubricant Layers by Sponge Application>

Tube was fabricated in the same manner as in example 1.

A sponge was soaked in the obtained liquid F. The tube was held from four directions and the sponge was moved over the tube in parallel to the length of the tube, thereby to coat the liquid F to the tube. After that, the tube was dried at 40° C. for six minutes to obtain the tube in which only the lubricant layer was formed on the surface of the tube.

The obtained tube was subjected to the foregoing evaluation tests. Table 2 shows evaluation results.

Comparative Example 2

Production of A Coating Liquid

Liquid F was prepared in the same manner as in comparative example 1.

<Formation of a Coating Layer by Dipping>

Tube was produced in the same manner as in example 1. The obtained liquid F was put into a dipping vessel (about 70 mm deep), and the foregoing tube was lowered at a constant speed of 5 mm/sec and a predetermined portion of the tube was dipped in the liquid F. Immediately after that, the tube was pulled out at the same speed in parallel to the length of the tube and then dried for five seconds at room temperature. The foregoing series of operations was repeated five times, and then the tube was dried at 40° C. for six minutes to obtain the tube in which only the lubricant layer was formed on the surface of the tube.

The obtained tube was subjected to the foregoing evaluation tests. Table 2 shows evaluation results.

Comparative Example 3

Production of A Coating Liquid

Liquid F was prepared in the same manner as in comparative example 1.

<Formation of a Coating Layer by Brush Application>

Tube was produced in the same manner as in example 1.

A brush was soaked in the obtained liquid F, the foregoing tube was held from four directions, and the brush was moved over the tube in parallel to the length of the tube, thereby coating the liquid F to the tube. After that, the tube was dried at 40° C. for six minutes to obtain the tube in which only the lubricant layer was formed on the surface of the tube.

The obtained tube was subjected to the foregoing evaluation tests. Table 2 shows evaluation results.

Comparative Example 4

Production of a Coating Liquid (1) Preparation of Liquid G

Liquid A was prepared in the same manner as in example 1.

The liquid A was blended 0.9 g with 0.6 g of ricinus oil and 8.5 g of THF, and was well stirred. Next, the liquid A was blended with 80 g of a solution with 10 weight % of THF in polyethylene glycol 20000, and stirred at 40° C. for three hours, thereby obtaining liquid G.

<Formation of a Coating Layer by Dipping>

Tube was produced in the same manner as in example 1. The obtained liquid G was put into a dipping vessel (about 70 mm deep), and the foregoing tube was lowered at a constant speed of 5 mm/sec and a predetermined portion of the tube was dipped in the liquid G. Immediately after that, the tube was pulled out at the same speed in parallel to the length of the tube and then dried for five seconds at room temperature. The foregoing series of operations was repeated five times, and then the tube was dried at 40° C. for six minutes to obtain the tube in which only the lubricant layer was formed on the surface of the tube. Table 2 shows evaluation results.

Comparative Example 5

Production of A Coating Liquid

Liquid F was prepared in the same manner as in comparative example 1. In addition, in the same manner as in (3) of example 1, a portion of the liquid F (1) was blended with THF for two-fold dilution, thereby preparing liquid F (1/2) in which the concentration of the coating composition was 5.3 weight %.

<Formation of a Coating Layer by Dipping>

A tube with an outer diameter of 1.0 mm and a length of 200 mm produced by Pebax was dipped in the obtained liquid F (1/2), and pulled out at a constant speed of 10 mm/sec in parallel to the length of the tube, and dried for one hour at room temperature, thereby obtaining the tube in which only the lubricant layer was formed on the surface of the tube.

The obtained tube was subjected to the foregoing evaluation tests. Table 3 shows evaluation results.

into a bent portion in a living body, for example. With regard to comparative examples 1 to 3, although there are differences in evaluation results of outer appearance in initial characteristics depending on the application methods, the results of friction load in initial characteristics were all favorable. Thus, none of the application methods exerted any influence on initial friction load, which suggests that the same results could be produced in the case of forming the double coating layer.

TABLE 1

|      |            | Liquid C (1) |       | Liquid D (1) |       | Liquid E | Liquid F |       | Liquid G |       | Liquid H |
|------|------------|-----|-------|-----|-------|-------|------|-------|------|-------|-------|
|      |            | [g] | [%]   | [g] | [%]   | [%]   | [g]  | [%]   | [g]  | [%]   | [%]   |
| (a)  | 4,4'-MDI*  | 0.39 | 12.0 | 0.10 | 3.7  | 6.8   | 0.85 | 8.9   | 0.59 | 6.2   | 8.2   |
| (b)  | Ricinus oil| 0.36 | 11.1 | 0.09 | 3.3  | 6.3   | 0.75 | 7.8   | 0.91 | 9.6   | 7.6   |
| (c1) | PEG4000    | 2.50 | 76.9 | 0   | 0     | 29.0  | 0    | 0     | 0    | 0     | 42.1  |
| (c2) | PEG35000   | 0    | 0    | 2.50 | 92.9 | 57.9  | 0    | 0     | 0    | 0     | 42.1  |
|      | PEG20000   | 0    | 0    | 0   | 0     | 0     | 8.00 | 83.3  | 8.00 | 84.2  | 0     |
|      | Sub total  | 2.50 | 76.9 | 2.50 | 92.9 | 86.9  | 8.00 | 83.3  | 8.00 | 84.2  | 84.2  |
|      | Total      | 3.25 | 100.0| 2.69 | 100.0| 100.0 | 9.60 | 100.0 | 9.50 | 100.0 | 100.0 |

*4,4'-diphenylmethane diisocyanate

TABLE 2

|            |                 |                   | Example 1 | Comparative Example 1 | Comparative Example 2 | Comparative Example 3 | Comparative Example 4 |
|------------|-----------------|-------------------|-----------|-----------------------|-----------------------|-----------------------|-----------------------|
|            | Application method |                | Sponge    | Sponge                | Dipping               | Brush                 | Dipping               |
| Evaluation item | Initial characteristics | Friction load | ○ | ○ | ○ | ○ | ○ |
|            |                 | Outer appearance  | ○         | ○                     | ○                     | X                     | ○                     |
|            | Durability      | Friction load     | ○         | ○                     | —                     | —                     | —                     |
|            |                 | Outer appearance  | ○         | X                     | X                     | X                     | X                     |

TABLE 3

|            |                         |                              | Example 3 | Comparative Example 5 |
|------------|-------------------------|------------------------------|-----------|-----------------------|
|            | Application method      |                              | Dipping   | Dipping               |
| Evaluation item | Initial characteristics | Friction load          | ○         | ○                     |
|            |                         | Outer appearance             | ○         | ○                     |
|            | Durability              | Transition of friction load After 100 reciprocations | 1.7 | 3.7 |
|            |                         | After 1000 reciprocations    | 2.5       | 4.9                   |

It can be understood from the comparison between example 1 and comparative example 1 and the comparison between example 3 and comparative example 5 shown in Tables 2 and 3, that the tubes with the double coating layer of intermediate layer and lubricant layer produced more excellent evaluation results than those of the tubes with only the lubricant layer, and thus the tubes with the predetermined intermediate layer were improved in durability. From the results of example 1, it can be expected that the tube in example 1 is applicable to medical catheters to be subjected to long-period placement in a living body. In addition, it can be expected from the results of example 3 that the tube in example 3 is applicable to medical catheters to be inserted

TABLE 4

|                         |                  | Intermediate layer coating liquid |         |        |
|-------------------------|------------------|-----------------------------------|---------|--------|
| Evaluation item         |                  | C(1/32)                           | C(1/16) | C(1/8) |
| Initial characteristics | Friction load    | ○                                 | ○       | ○      |
| Durability              | Friction load    | ○                                 | ○       | ○      |
|                         | Outer appearance | ○                                 | ○       | ○      |

It can be understood from Table 4 that favorable durability can be achieved when the lubricant layer coating liquid is higher in concentration than the intermediate layer coating liquid.

REFERENCE SIGNS LIST

1 Lacrimal duct tube
2a First bougie
2b Second bougie
3 Mark
4 Central part
5a First cylindrical part
5b Second cylindrical part
6 First terminal end
7 Cut for insertion of bougie
8 Second terminal end
21 Upper lacrimal punctum
22 Lower lacrimal punctum
23 Upper lacrimal canaliculus
24 Lower lacrimal canaliculus
25 Common canaliculus
26 Lacrimal sac
27 Nasolacrimal duct
28 Inferior nasal meatus
30 Occlusion catheter
31 Inner tube
32 Outer tube
33 Balloon
34 Hub
35 Balloon lumen
36 Luminal part
37 Inner layer
38 Outer layer
39 Base material
40 Coating layer
41 First opening part
42 Second opening part
43 Luminal part

The invention claimed is:

1. A medical tube in which an intermediate layer comprising a dried composition containing (a), (b), and (c1) listed below and a lubricant layer comprising a dried composition containing (a), (b), and (c2) listed below are sequentially laminated on a surface of an insertion member to be inserted into a living body:
(a) 1 to 35 weight % of aromatic diisocyanate;
(b) 1 to 18 weight % of trifunctional or higher functionality polyol;
(c1) 47 to 98 weight % of polyalkylene glycol having a weight-average molecular weight of 2000 or more and 6000 or less; and
(c2) 47 to 98 weight % of polyalkylene glycol having the weight-average molecular weight of 20000 or more and 40000 or less, where each of the glycols in (c1) and (c2) is diol.

2. The medical tube according to claim 1, wherein component (c2) includes 10 to 50 weight % of the component (c1).

3. The medical tube according to claim 1 or 2, obtained by coating and drying an intermediate layer coating liquid containing the components (a), (b), (c1) and a solvent, and a lubricant layer coating liquid containing the components (a), (b), (c2) and a solvent, wherein the concentration of the total amount of the components (a), (b), and (c1) in the intermediate layer coating liquid is equal to or less than total the concentration of the total amount of the components (a), (b), and (c2) in the lubricant layer coating liquid.

4. The medical tube according to claim 3, wherein
the concentration of the total amount of the components (a), (b), and (c1) in the intermediate layer coating liquid is 0.1 to 10 weight %, and
the concentration of the total amount of the components (a), (b), and (c2) in the lubricant layer coating liquid is 1.0 to 10 weight %.

5. The medical tube according to claim 1, wherein a composition of the intermediate layer contains a pre-polymer formed by pre-reaction of at least part of the components (a), (b), and (c1) and/or a composition of the lubricant layer contains a pre-polymer formed by pre-reaction of at least part of the components (a), (b), (c1), and (c2).

6. The medical tube according to claim 1, wherein the composition of the intermediate layer is a reaction product obtained by reaction of the components (a), (b), and (c1), and/or the composition of the lubricant layer is a reaction product obtained by reaction of the components (a), (b), (c1), and (c2).

7. The medical tube according to claim 1, wherein a material for the insertion member comprises at least one selected from a group consisting of silicon resin, isobutylene block copolymer, thermoplastic polyurethane resin, and polyamide resin.

8. The medical tube according to claim 1, wherein the medical tube is a lacrimal duct tube to be inserted into a lacrimal duct and to be placed in the same.

9. The medical tube according to claim 8, wherein the material for the insertion member comprises a thermoplastic polyurethane resin and an isobutylene block copolymer.

10. A production method of the medical tube according to claim 1, comprising the steps of:
preparing an intermediate layer coating liquid containing the components (a), (b), (c1) and a solvent; and
preparing a lubricant layer coating liquid containing the components (a), (b), and (c2) and a solvent, so as to contain 10 to 50 weight % of the intermediate layer coating liquid.

11. The production method of the medical tube according to claim 10, comprising the steps of:
coating the intermediate layer coating liquid containing the components (a), (b), (c1) and the solvent on the insertion member;
drying the intermediate layer coating liquid;
coating the lubricant layer coating liquid in which the concentration of the total amount of the components (a), (b), and (c2) is equal to or larger than the concentration of the total amount of the components (a), (b), and (c1) of the intermediate layer coating liquid; and
drying the lubricant layer coating liquid, thereby to laminate in sequence the intermediate layer and the lubricant layer on the surface of the insertion member.

12. The production method of the medical tube according to claim 11, wherein
the concentration of the total amount of the components (a), (b), and (c1) in the intermediate layer coating liquid is 0.1 to 10 weight %, and
the concentration of the total amount of the components (a), (b), and (c2) in the lubricant layer coating liquid is 1.0 to 10 weight %.

13. The production method of the medical tube according to any of claims 10 to 12, wherein comprising the steps of coating the intermediate layer coating liquid and/or the lubricant layer coating to the placement member is dipping, coating by a sponge including the intermediate layer coating liquid and/or the lubricant layer coating, coating by a brush including the intermediate layer coating liquid and/or the lubricant layer coating, or spraying.

14. The medical tube according to claim 1, wherein
the intermediate layer including the composition that contains the (a) in an amount of 5 to 30 weight %.

15. The medical tube according to claim 1, wherein
the intermediate layer including the composition that contains the (b) in an amount of 3 to 25 weight %, and
the lubricant layer including the composition that contains the (b) in an amount of 2 to 25 weight %.

16. The medical tube according to claim 1, wherein
the intermediate layer including the composition that contains the (c1) in an amount of 40 to 95 weight %.

17. The medical tube according to claim 1, wherein
the lubricant layer including the composition that contains the (c2) in an amount of 40 to 95 weight %.

18. The medical tube according to claim 1, wherein
the amount of the aromatic diisocyanate (a) is 3 to 35 weight %.

19. The medical tube according to claim 1, wherein
the amount of the aromatic diisocyanate (a) is 5 to 20 weight %,
the amount of the trifunctional or higher functionality polyol (b) is 3 to 15 weight %,
the amount of the polyalkylene glycol (c1) is 50-98 weight %, and
the amount of the polyalkylene glycol (c2) is 50-98 weight %.

* * * * *